(12) United States Patent
Streit et al.

(10) Patent No.: US 11,534,556 B2
(45) Date of Patent: Dec. 27, 2022

(54) MONITORING AN INJECTION PROCESS

(71) Applicant: Ypsomed AG, Burgdorf (CH)

(72) Inventors: Ursina Streit, Schönbühl (CH); Leos Urbanek, Bern (CH); Michael Gentz, Burgdorf (CH); Jonas Rihs, Orpund (CH)

(73) Assignee: Ypsomed AG, Burgdorf (CH)

( * ) Notice: Subject to any disclaimer, the term of this patent is extended or adjusted under 35 U.S.C. 154(b) by 301 days.

(21) Appl. No.: 16/585,073

(22) Filed: Sep. 27, 2019

(65) Prior Publication Data

US 2020/0023139 A1   Jan. 23, 2020

Related U.S. Application Data

(63) Continuation of application No. PCT/IB2018/052114, filed on Mar. 28, 2018.

(30) Foreign Application Priority Data

Mar. 30, 2017 (EP) ..................................... 17163755

(51) Int. Cl.
*A61M 5/31* (2006.01)
*A61M 5/315* (2006.01)

(52) U.S. Cl.
CPC ...... *A61M 5/31568* (2013.01); *A61M 5/3155* (2013.01); *A61M 5/3158* (2013.01);
(Continued)

(58) Field of Classification Search
CPC ............ A61M 5/31568; A61M 5/3155; A61M 5/3158; A61M 2005/3126
See application file for complete search history.

(56) References Cited

U.S. PATENT DOCUMENTS

| 8,845,557 | B1 * | 9/2014 | Giuffrida | A61B 5/4839 |
| | | | | 600/595 |
| 2012/0053527 | A1 * | 3/2012 | Cirillo | G01F 15/061 |
| | | | | 604/189 |

(Continued)

FOREIGN PATENT DOCUMENTS

| EP | 2182456 A1 | 5/2010 |
| EP | 2812055 A1 | 12/2014 |

(Continued)

OTHER PUBLICATIONS

"International Preliminary Report on Patentability", received for International Application No. PCT/IB2018/052114, dated Oct. 1, 2019, 7 pages.

(Continued)

*Primary Examiner* — Nathan R Price
*Assistant Examiner* — Courtney B Fredrickson
(74) *Attorney, Agent, or Firm* — Dorsey & Whitney LLP (57) ABSTRACT

Shown is a simple, reliable manner of monitoring a process of expelling a variable dose of medicament from an injection device by analyzing mechanical feedback of the injection device with reduced requirements on signal data memory space and processing power. Specific measurand and mechanical user feedback sensor configurations enable sensor signal data from which individual dosage units of expelled drug are identifiable at moderate sampling rates. Preferred configurations include a force sensor adapted to measure an axial force component as applied to the device by a user pressing a proximal injection button, and a direction sensor adapted to measure an azimuth angle of an orientation of the device. The specific measurands, or process quantities observed, relate to feedback means of the device including a resilient element that produces a number of successive mechanical feedback events proportionate to a (Continued)

dose or quantity of drug expelled from a medicament reservoir.

13 Claims, 4 Drawing Sheets

(52) U.S. Cl.
CPC .............. *A61M 2005/3126* (2013.01); *A61M 2205/0294* (2013.01); *A61M 2205/332* (2013.01); *A61M 2205/3327* (2013.01); *A61M 2205/3584* (2013.01); *A61M 2205/50* (2013.01); *A61M 2205/582* (2013.01); *A61M 2205/587* (2013.01)

(56) References Cited

U.S. PATENT DOCUMENTS

| | | | | |
|---|---|---|---|---|
| 2015/0206456 A1* | 7/2015 | Foster | ................. | G09B 23/285 434/262 |
| 2015/0246179 A1* | 9/2015 | Zur | ........................ | G16H 20/17 604/506 |
| 2016/0129182 A1 | 5/2016 | Schuster et al. | | |
| 2016/0213853 A1* | 7/2016 | Despa | ............... | A61M 5/31568 |
| 2017/0182258 A1* | 6/2017 | Michael | ............ | A61M 5/31568 |

FOREIGN PATENT DOCUMENTS

| | | |
|---|---|---|
| WO | 2007107564 A1 | 9/2007 |
| WO | 2012046199 A1 | 4/2012 |
| WO | 2015071354 A1 | 5/2015 |
| WO | 2016118736 A1 | 7/2016 |

OTHER PUBLICATIONS

"International Search Report and Written Opinion", received for International Application No. PCT/IB2018/052114, dated Jul. 4, 2018, 9 pages.

Extended European Search Report issued in European Patent Application 17163755.6 dated Oct. 9, 2017, 7 pages.

* cited by examiner

MONITORING AN INJECTION PROCESS

CROSS-REFERENCE TO RELATED APPLICATIONS

This application is a continuation of International Application No. PCT/IB2018/052114 filed Mar. 28, 2018, which claims priority to European Application No. 17163755.6, filed Mar. 30, 2017, the entire contents of all of which are incorporated by reference herein in their entirety.

FIELD OF THE INVENTION

The present invention relates to injection devices or medicament delivery devices for injecting, delivering, administering, infusing or dispensing substances and/or liquids such as insulin or hormone preparations. It starts from an electronic unit incorporated in, or attachable to, an injection device, and comprising a sensor for monitoring an injection process executed by means of the injection device.

BACKGROUND

A variety of diseases exist that require regular treatment by subcutaneous injection of a medicament. By way of example, type-1 and type-2 diabetes can be treated by injection, or administration, of insulin doses, either once or several times per day. Such injections can be performed with the help of injection devices that may be handled by the patients themselves. Typical injection devices include pre-filled multi-dose disposable insulin pens and re-usable insulin pens that allow replacement of an empty medicament container or cartridge by a new one. The insulin dose to be injected may typically be manually selected by turning a dosage knob and observing the actual dialed dose from a dose window or display of the insulin pen. A dose is dispensed by inserting the needle into a suited portion of human skin and by pressing an injection or release button of the insulin pen. In order to monitor the injection of insulin, for instance to prevent false handling of the insulin pen or to keep track of the doses already applied, it is desirable to measure and process information related to a use of the injection device, such as information on the injected insulin type, dose, and circumstances of an injection process.

WO 2007/107564 proposes to record acoustic signals or vibration signals that may allocated, in particular, to a dose delivery of the medication or to a dose adjustment process. If a detected "click-sound" falls within a low frequency range, a unit dose of medicament is being set. Similarly, if the detected "click-sounds" fall within a high frequency range a dose of medicament is being expelled from the medication delivery device. By counting the number of clicks during an expel sequence the amount of medicament expelled from the medicament delivery device can easily be calculated.

WO 2016/118736 discloses an injection device such as an insulin pen designed to produce an audible or tactile feedback to a user every time a dose unit is dialed or selected.

Within the injection device, a sudden release of mechanical energy results in overall motion and vibrations transmitted through the injection device body or internal volumes of air, and manifests to the user through audible clicks and tactile feedback. Sensors are configured to detect such release of mechanical energy, and a microprocessor is configured to analyze data from the sensors to identify dose increasing dialing events and dose decreasing dialing events, and to distinguish dose dialing events from an accidental knock of the injection device or from an injection event. In specific embodiments, sensor data is collected at a 30 kHz sampling frequency from a single axis accelerometer, with a low frequency component of less than 100 Hz being notably different for increase and decrease dose dialing events, and with a high frequency component including frequencies greater than 4 kHz representing a click sound.

US 2016129182 proposes to compare a time waveform and/or frequency spectra of a vibration signal to pre-loaded analysis results related to previous or expected time waveforms and/or frequency spectra, to identify one of setting a desired dose or delivery of a set dose. Dose amounts are determined by counting vibrations associated with 1 IU or 0.5 IU of insulin. Vibration sensors respond to accelerations or velocities due to various types of oscillations, including shear, flexural, and surface oscillations. The vibration sensor may be an accelerometer comprising, for example, piezoelectric, piezo-resistive and/or capacitive components and/or may include a MEMS (Micro Electro-Mechanical System) device or component.

EP 2182456 A1 discloses an electronic module coupled to a medication delivery device, the electronic module comprising one of a piezoelectric sensor, pressure sensor, vibration sensor, touch contact sensor or distance sensor, to detect axial vibration signals arising from operation such as priming or expelling events of the delivery device. Signals generated in response to a measurable operation of the delivery device are detected in an electronic module coupled to a dosing knob at a proximal end of the delivery device.

The above prior art approaches focus on a detection of a set dose or of an expelled dose in variable-dose injection devices by way of identifying and counting individual dosage units in a vibration pattern involving frequencies in the audible range and beyond. Reliably identifying individual clicks in a vibration signal as output by a conventional accelerometer requires the digital time-discrete accelerometer output signal to be available at an elevated resolution or sampling frequency. This in turn increases the requirements on data storage memory and processing power. Exploring alternative mechanical properties of the injection device and corresponding data collection processes in view of a subsequent identification of individual dosage units may thus be beneficial.

In the following context, the term "injection device" refers to a generally pen-shaped device with an elongate device body defining a longitudinal main device axis. The term "distal end" refers to the end of the injection device where an injection needle is located, the term "proximal end" designates the opposite end thereof.

In the present context, the terms "substance", "drug", "medicament" and "medication" are to be understood to include any flowable medical formulation suitable for controlled administration through a means such as, for example, a cannula or a hollow needle, and comprises a liquid, a solution, a gel or a fine suspension containing one or more medical active ingredients. A medicament can be a composition comprising a single active ingredient or a pre-mixed or co-formulated composition with more than one active ingredient present in a single container. Medication includes drugs such as peptides (e.g., insulin, insulin-containing drugs, GLP-1 containing drugs or derived or analogous preparations), proteins and hormones, active ingredients derived from, or harvested by, biological sources, active ingredients based on hormones or genes, nutritional formulations, enzymes and other substances in both solid (suspended) or liquid form but also polysaccharides, vaccines, DNA, RNA, oligonucleotides, antibodies or parts of antibodies but also appropriate basic, auxiliary and carrier substances.

SUMMARY OF THE INVENTION

It is an objective to enable secure, easy and cost-effective operation of components, devices and systems for the generation, collection and distribution of data associated with the handling or use of injection devices. It is an objective to monitor, in a simple, reliable manner, a process of expelling a variable dose of medicament from an injection device by way of analyzing mechanical feedback of the injection device with reduced requirements on signal data memory space and processing power. These objectives are achieved by a method of monitoring an injection process and an electronic unit according to the independent claims. Preferred embodiments are evident from the dependent patent claims.

According to the embodiments, specific measurand and mechanical user feedback sensor configurations allow to produce sensor signal data from which individual dosage units of expelled drug are identifiable at moderate sampling rates. Preferred configurations include a force sensor adapted to measure an axial force component as applied to the injection device by a user pressing a proximal injection button, and a direction sensor adapted to measure an azimuth angle of an orientation of the injection device. The specific measurands, or process quantities observed, relate to operation of user feedback means of the injection device including a resilient element that produces a number of successive mechanical feedback events proportionate to a dose or quantity of drug expelled from a reservoir of the injection device. Specifically, the measurands allow to identify a user feedback preparatory activity preceding a feedback event perceptible by the user. The preparatory activity includes charging, or straining, of a resilient element such as a spring (i.e., loading it with potential energy) and/or maintaining the resilient element in a charged (or loaded) state, which translates into a gradually increasing and/or an at least approximately constant axial force component. The feedback event, on the other hand, includes release and discharge of the resilient element, acceleration of a feedback element by the discharging resilient element, and abutment of the accelerated feedback element against a stationary device part to generate a click sound and/or a vibration burst. Measured sensor signal data at a sampling frequency below a threshold of one kilohertz still enables identifying of the low-frequency preparatory activities. Accordingly, the oscillations related to the click sound or solid state vibration burst generated by the relaxing resilient element may be disregarded in, or filtered from, the sensor signal data.

In the context of the present invention, any step or activity designated as measuring or recording an exemplary force or acceleration component may include one or several of the steps including capturing the quantity with a mechanical feedback sensor to generate an output signal, sampling or digitizing the output signal to generate a discrete-time signal, analog and/or digital integration of a signal, analog and/or digital filtering of a signal by appropriate high-, low-, band-pass or notch filters, compressing, equalizing and/or otherwise processing a signal, and storing a discrete-time signal in a data memory. These steps may be performed by appropriate processing means of the feedback sensor itself, or by a dedicated processing unit wired to the sensor.

According to the invention, a method of monitoring an injection process executed by means of an elongate injection device with a main axis includes the step of measuring, during a drug expel process, an axial force profile of the expel process. The method further includes the step of identifying, in the axial force profile, successive intervals with a force profile attributable, or corresponding, to respective instances of a user feedback preparatory activity that includes charging (loading) of a resilient element and/or maintaining the resilient element in a partly and/or fully charged (loaded) state. The method concludes with a step of counting the number of identified intervals, or equivalently, the number of dosage unit expelling events, in the force profile to determine an expelled dose. Optionally, the determined expelled dose is time-stamped and stored in a memory connected to the processing unit.

The interval is representative of an inter-click state of the injection device in-between successive clicks or vibration bursts caused by the resilient element being released and discharged. The force profile is determined by a force sensor or transducer, and includes a time-variable force component in the direction of the main axis of the injection device. The interval identification is executed by a processing unit connected to the force sensor and receiving the force profile as time-discrete digital sensor data. The sensor data is suitably filtered and integrated to retain, or reproduce, the intervals of interest, while possibly reducing the large amplitude high frequency mechanical oscillations that may be captured upon release of the resilient element, and abutment of a feedback generating element of the feedback means accelerated by the relaxing resilient element. Sensor data may thus be collected and/or prepared at a sampling rate adapted to the number of expelled dosage units per second rather than to the vibration frequencies, hence the sampling rate may be anywhere between a lower limit of two and an upper limit of ten times the frequency of the expelled dosage units. Specifically, the sampling rate may be limited to values below 1 kHz, below 500 Hz, below 200 Hz, and even below 100 Hz. The origin of the mechanical feedback, specifically the distinction between a dialing click and an expel click, may be established by the processing unit from the axial force profile and/or from another measurand or process quantity observed.

In a preferred embodiment, the charging (loading) of the resilient element includes moving the feedback element in a first direction or along a first path against a restoring or opposing force of the resilient element. At the end of the interval, the feedback element is accelerated by the relaxing resilient element to abut, or hit, a stationary part of the injection device. The first direction may be axial, or parallel to the main axis, for instance in case the resilient element is a co-axially arranged spring. Alternatively, the first direction or path may include a radial component, i.e. a variable distance between the feedback element and the device axis in a plane perpendicular to the axis. This is the case if the resilient element is an essentially two-dimensional or flat spiral spring, or at least comprises a flexible arm rotatable around the axis and carrying a tooth, cam, or other feedback element that engages with circumferentially arranged stationary counterpart teeth.

In a preferred embodiment the injection device includes dosing means for setting a dose of drug to be expelled, including a dosing click spring for generating a number of mechanical feedback events proportionate to a set or adjusted dose of drug to be expelled from the injection device. The method further comprises the step of measuring, by the force sensor, an axial force profile of a dose dialing or dose adjustment process or operation. The method further includes the step of identifying, in the dose dialing force profile, intervals attributable to a charging of the dosing click spring and/or to a charged state of the dosing click spring preceding a dosing click, and concludes with a step of counting the number of identified dialing or adjusting events. Accordingly, a dose volume or quantity to be expelled from the injection device may be determined prior to, and independently of, the aforementioned steps of determining an actually expelled dose.

In a further advantageous variant, a wireless communication unit is connected to the processing unit, and adapted to wirelessly communicate, specifically upload, injection information to a nearby mobile device. The injection information includes at least a time stamp and the expelled dose, indicative of a time and quantity of injected medication, and optionally a dialed and/or corrected dose. The injection information may be transmitted instantaneously, or stored in a memory unit connected to the processing unit, for later upload or batch transfer. The injection information may, in addition or alternatively, include a quality measure of an injection process, such as a binary flag indicating that a determined dialed dose corresponds to a determined expelled dose.

An electronic unit comprising a mechanical feedback sensor and a processing unit is adapted to cooperate with an injection device generating a tactile feedback during an injection process, and configured to execute some or all of the aforementioned method steps. The electronic unit may be integrated in the injection device and hence disposed of together with the injection device. For reusable injection devices with cartridge replacement, this will be the case after expiry of a certain minimum lifetime of the injection device. On the other hand, the electronic unit may advantageously be part of a reusable electronic module that attaches to a disposable mechanical injection device in a detachable or removable way, for monitoring of an injection process executed by a user by means of the injection device. This is of particular interest in retrofit configurations with an existing injection device design that is not available for adaptations such as incorporation of an electronic unit.

An electronic module including the electronic unit has a dedicated module housing adapted to be attached, by means of a releasable locking mechanism, to an injection device part such as a device housing or a discharge button, and is designed to avoid obstruction of other interface elements of the injection device, specifically of a dosing knob. The electronic module is adapted to detect and exploit mechanical feedback signals emanating from the injection device, and may expressly exclude the presence of any further optical and/or electrical sensor for monitoring the use of the injection device. Other kinds of interaction between the electronic module and the injection device may independently be present or be excluded. For instance, a mechanical keying element of the electronic module may interact with dedicated counterpart keying element provided on the injection device to disable activation preventing elements of the injection device, as a prerequisite for a proper use of the injection device.

The electronic unit being integrated in the injection device or being part of an electronic module may comprise a visual, audible and/or tactile status indicator, indicating to a user a status of the system. The status of the system may include any of a device status of the injection device, a module status of the electronic module, or a process status of an overall injection process or injection device handling process. The status indicator may be simple and limited to a few Light Emitting Diodes LEDs in traffic-light colors and/or an audible signal generator for generating language-independent beep sounds or simple melodies. The status indicator may explicitly exclude any advanced human-machine interfacing capability, and be limited to a few, specifically less than ten, messages conveyable to the user. In particular, the electronic unit may not be wired to, and the electronic module may be devoid of, a display, screen, or projector for visually transmitting readable instructions, and likewise exclude an artificial speech assistant for reading out loud the instructions. Such advanced HMI functionality including elaborate graphic display and speech output capabilities are preferably being provided by a mobile device communicatively connected to the electronic unit. The status information may be redundant or complementary to primary signals from the injection device that a user may still capture in parallel. In particular, the status information may include a positive confirmation of a dose having been set or corrected, or an indication about a lapse of a minimum holding, delay, or dwell time following completion of a substance expel or piston forwarding activity to inform the user that it is now safe to remove the injection device.

An electronic unit for monitoring a drug expel process performed by means of an injection device comprises an orientation sensor and a processing unit connected to the orientation sensor. The orientation sensor is adapted to measure, and output a signal dependent on, an azimuth angle of a main axis of the injection device. In other words, the orientation sensor determines an orientation of the injection device relative to a reference direction in a plane perpendicular to the direction of gravity. The processing unit is configured to receive the azimuth signal output by the orientation sensor and identify a dosage unit expelling event there from. The processing unit is further configured to count the number of dosage unit expelling events to determine an expelled dose. The step of identifying dosage units may include identifying, in the azimuth angle profile, intervals attributable to a charging (loading) of a resilient element and a charged (loaded) state of the resilient element, and/or vibrations subsequently generated by the discharging resilient element.

Preferably, the azimuth angle sensor output signal data is prepared at a sampling rate of less than 4 kHz, less than 2 kHz, or even less than 1 kHz. A gyroscope or gyroscopic sensor may be used as an orientation sensor to detect vibrational movement of the injection device in a plane perpendicular to the direction of gravity, and thus produce an indication about an azimuth direction relative to a reference direction. Contrary thereto, an accelerometer which measures proper acceleration, which is the acceleration experienced relative to freefall and felt by people and objects, may only be used for orientation sensing relative to the direction of gravity. Reverting to a gyroscopic orientation sensor other than a conventional accelerometer is particularly helpful for injection devices with tactile feedback generating elements that rotate around a device axis and feature wedge shaped teeth which in turn do give rise to oscillating tangential force components.

In a preferred embodiment, the orientation sensor is a multiple-axis gyroscope, specifically a three-axis gyroscope producing concurrently three output signals indicative of an absolute orientation of the injections device. Vibrating structure gyroscopes manufactured with Micro Electro-Mechanical System (MEMS) technology are readily available, may provide either analog or digital outputs, and in many cases effectively include gyroscopic sensors for multiple axes.

BRIEF DESCRIPTION OF THE DRAWINGS

The subject-matter of the invention will be explained in more detail in the following text with reference to preferred exemplary embodiments as illustrated in the attached drawings, of which

For consistency, the same reference numerals are used to denote similar elements illustrated throughout the drawings.

DETAILED DESCRIPTION

Figure 1:
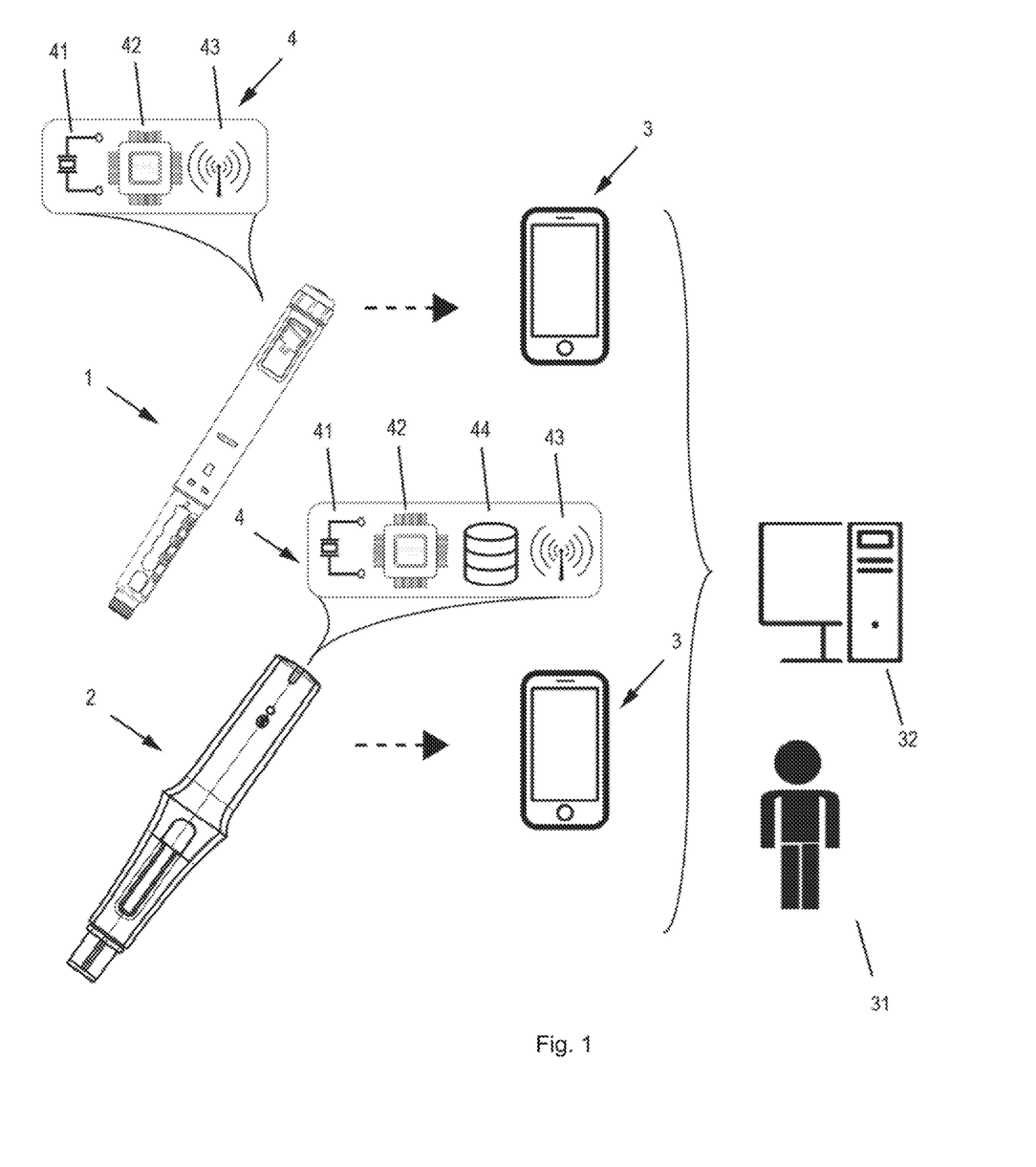
FIG. 1 depicts two variants of a medical injection monitoring and patient support system.

FIG. 1 depicts two variants of a medical injection monitoring and patient support system, each variant comprising an injection device 1, an electronic unit 4 and a mobile device 3 such as a smartphone or tablet device running a dedicated application program; or a laptop computer configured accordingly. The mobile device of each variant is adapted to interact with a respective patient 31 as well as a remote server, cloud based computing facility, or expert system 32. In variant one (FIG. 1 top), an electronic unit 4 is embedded, or incorporated, in the injection device. In variant two (FIG. 1 bottom), the electronic unit is part of an electronic module 2 that in turn is detachably mounted on the injection device. In both variants one and two, the electronic unit comprises a mechanical feedback (i.e. force or gyroscopic) sensor 41, a processing unit 42 and a transmitter unit 43 for wireless transmission of data about the injection progress via Bluetooth Low Energy (BTLE) or equivalent short or near range wireless communication technology to the mobile device as indicated by the dashed horizontal arrows. The electronic module of variant two additionally includes a data storage unit 44.

In both variants, the electronic unit 4 may be adapted to measure, during a drug expel process, an axial force profile of the expel process, and to identify, in the axial force profile, intervals with a force profile attributable to a charging (loading) of a resilient element. The electronic unit is further adapted to count the number of identified intervals, or equivalently, the number of dosage unit expelling events, in the force profile in order to determine an expelled dose or quantity. The exemplary electronic unit of variant two is further adapted to produce a time-stamp indicating at what date and time the dose has been injected, and to store at least the dose expelled and the time-stamp in a memory connected to the processing unit.

Figure 2A:
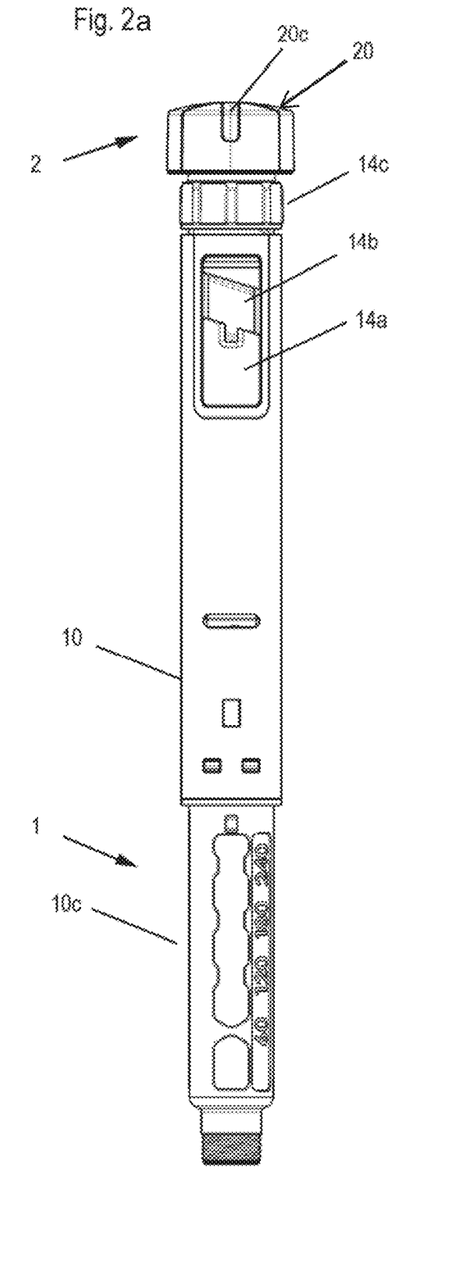
FIGS. 2a and 2b depict side and cross-sectional views (respectively) of an injection device with one embodiment of a detachable electronic module.
Figure 2B:
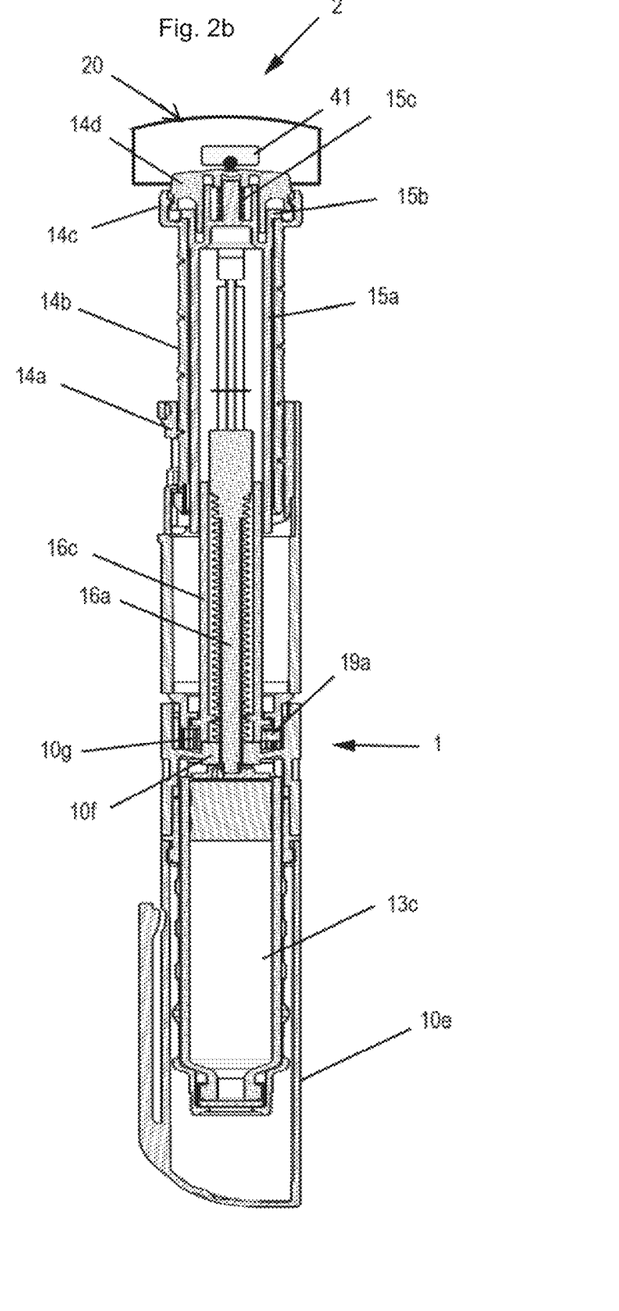

FIGS. 2a-2b depict a variable dose injection device 1 with a dose dialing facility as amply described for instance in EP 2812055. The housing 10 forms the base of the pen-shaped injection device and is fixed to a carpule holder 10c containing a carpule or cartridge 13c by means of a snap connection. Dosing and delivery components are at least partially arranged in the housing. An indicator sleeve 14a is rigidly inserted into the housing 10 and has an internal thread, to which a thread on an outer surface of a dosing sleeve 14b is engaged. The rotary dosing knob 14c for enabling the user to adjust a dose is arranged on the proximal end of the dosing sleeve. The dosing sleeve features markings in the form of numbers on its outer surface. When the dosing sleeve is screwed out of the housing during the dosing operation, the adjusted dose is displayed in the window 10a. On the proximal end of the injection unit, a discharge button 14d is snapped on the dosing sleeve in such a way that the discharge button can slightly move axially relative to the dosing sleeve and is freely rotatable.

The left-hand part, FIG. 2a, depicts in more detail a first embodiment of the specific monitoring system of aforementioned variant two, with the electronic unit comprised in an electronic module 2. The pen-shaped injection device 1 has an elongate housing 10 essentially symmetric around a main axis. The electronic module has a hollow module housing 20 forming a cavity or inner space adapted to an outer shape of the proximal end of the injection device. The electronic module is affixed to the discharge button 14d, and only has a limited extension in axial direction overlapping the injection device, such that the dosing knob 14c may still be accessed by a user of the device. The module housing may extend further in distal direction provided that it is designed to be positioned on the injection device housing in such a way as to neither interfere with the dial-and-dose components nor obscure any display window or visual indicator of the device. Included in the module housing 20 is a lock/release mechanism to secure the attachment of the electronic module to the injection device in order to protect against unintended detachment. Connection and system status indicator 20c (FIG. 4) provides visual feedback about a connection status indicative of an established communication link to a mobile device, and about a device, module, or process status including for instance an availability of battery power, a readiness of communication means, an attached/detached status of the electronic module and the injection device, or a progress of an ongoing injection process. A detachable, reusable electronic module preferably is adapted for a sustained use during an intended lifetime, with corresponding requirements including a cleanable and waterproof, at least splash water protected, module housing.

FIG. 2b shows a longitudinal section through the variable dose injection device 1 in an initial state, after dose selection but prior to removal of a device cap 10e. In order to increase legibility, the section has been drawn with a scale and aspect ratio different from the one in the left-hand drawing. A mechanical feedback sensor in the form of a force sensor 41 is incorporated or integrated, as a part of the electronic unit, into the electronic module 2. Any axial force exerted on the electronic module by the thumb of a user is directed through the force sensor to the discharge button. Suitable force sensors are based on a piezo-resistive effect, i.e. on a change of resistivity of a conductor upon mechanical deformation. Force sensors may convey an applied force between zero and 20 Newton across an actuator ball directly to a Si-based MEMS with integrated piezo-resistive elements, with the ball translating less than 50 micrometers. Alternative force sensors for measuring static forces include strain gauges or Force Sensing Resistors (FSR).

FIG. 2b, further shows a coupling sleeve 15a arranged coaxial to the dosing sleeve 14b. Close to its proximal end the coupling sleeve comprises an annular flange 15b that engages, via a distally oriented toothing comprising an exemplary number of twenty teeth evenly distributed about the circumference, with a complementary annular counter-face of the dosing sleeve. A dosing click-spring 15c is arranged between the discharge button 14d and the coupling sleeve. Due to the snap-on connection between the discharge button and the dosing sleeve, the annular flange and the counterface are pressed against one another. Turning the dosing knob 14c of the dosing sleeve in a dose-increasing, clockwise dialing direction or in a dose-reducing, counter-clockwise corrective direction relative to the coupling causes the toothing of the counterface to slide over the toothing of the flange, repeatedly performing a slight axial back and forth motion that gives rise to a clicking sound and vibration burst at every tooth. The number of clicks is proportionate to the dosage volume, wherein preferably each click or vibration burst corresponds to a single dosage unit, such as an International Unit IU. A relative rotation between the coupling sleeve and the dosing sleeve is inhibited when the discharge button is manually pressed in the distal direction against the spring force. A force sensor adapted to detect modulations of the force or pressure in axial direction due to the relative sliding of the toothings is preferably incorporated in the injection device and located in series with the dosing click-spring between discharge button and dosing knob, or between discharge button and coupling sleeve.

A sleeve-shaped threaded nut 16c is axially fixed in the housing and rotationally coupled to the coupling sleeve 15a. On its inner side, the threaded nut features a thread that is engaged with the external thread of a piston rod 16a. The piston rod is axially guided by a piston rod guide 10f of the device housing. On a distal end, the threaded nut is provided with a flexible arm 19a having one end solidly anchored in the threaded nut and carrying a tooth, or cam, at a second, free end of the arm. The tooth may radially move or flex in a plane perpendicular to the axis such that the distance between the tooth and the axis varies. The flexible arm is biased radially outward such that the tooth arranged thereon engages with a grating 10g on the inner side of the housing. The flexible arm, the tooth and/or the grating are shaped in such a way that the threaded nut can only rotate in a direction which results in a motion of the piston rod in the distal, dose-expelling direction. Since the threaded nut rotates relative to the housing during the discharge, the tooth of the flexible arm also rotates relative to the grating, which in turn generates a mechanical, i.e. acoustic and tactile discharge feedback signal to the user. A plurality of, such as two or four, flexible arms with corresponding teeth may be provided, wherein the grating is designed such that an exemplary number of twenty time-wise distinct flex-back movements of the flexible arm(s) take place in one turn of the threaded nut. Each flex-back movement generates a mechanical feedback indicative of a dosage unit, or fraction thereof, being expelled, and involves one or several of the flexible arms discharging (i.e., releasing energy stored in a flexed state) to abut against a bottom part of the grating.

Figure 3:
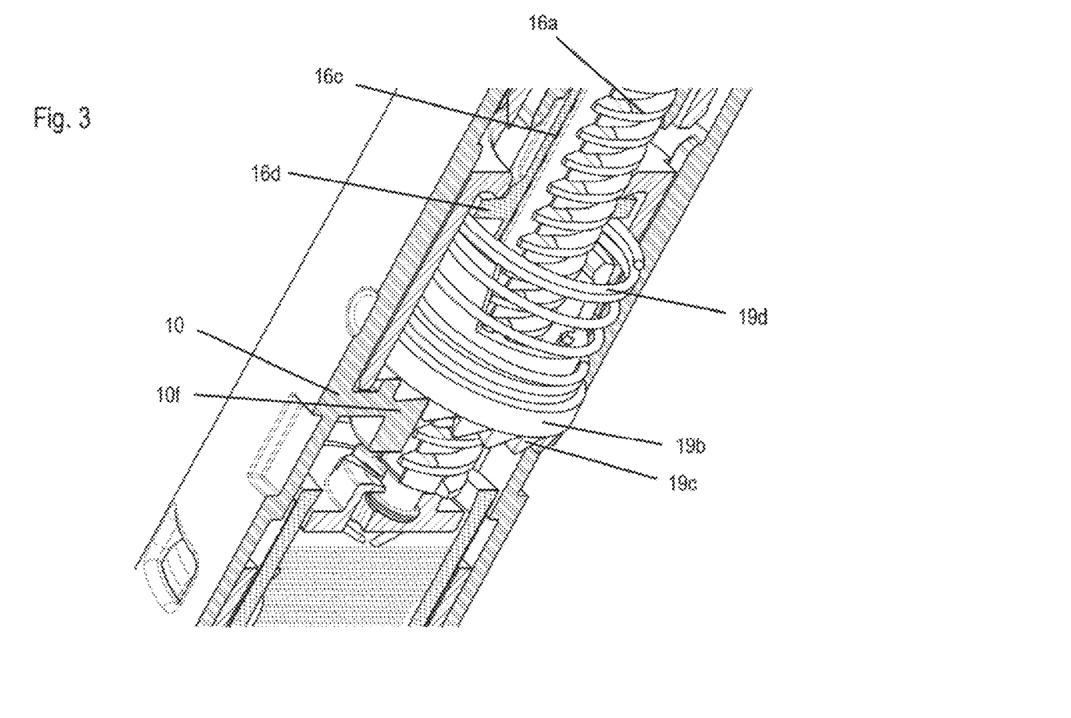
FIG. 3 depicts an injection device with an alternative reverse lock.

FIG. 3 depicts an alternative to the flexible arms of FIG. 2b that likewise operates as a reverse lock ensuring that the threaded nut 16c can only be rotated or turned relative to the housing in one direction. On its distal end, the threaded nut 16c is surrounded by an annular toothed disk 19b. The toothed disk can be longitudinally displaced relative to the threaded nut, but is secured against rotating relative to the threaded nut and arranged coaxial thereto.

The toothed disk comprises a toothing 19c with an exemplary number of twenty teeth evenly distributed over the circumference and protruding in distal direction. These teeth engage into a counter-toothing on the piston rod guide 10f of the device housing under the effect of a resilient element in the form of a co-axial expel click spring 19d supported on flange 16d of the threaded nut. Upon rotation of the threaded nut and toothed disk the toothing of the disk slides over the counter-toothing of the housing in a combined rotational and axial movement against the force of the expel click spring, repeatedly interrupted by an axial return motion in distal direction. The latter includes a linear acceleration of the toothed disk by the relaxing click spring, until the disk abuts against the counter-toothing to give rise to a click sound and vibration burst. The toothing is advantageously realized asymmetrically such that a relative rotation between the toothed disk and the housing is possible in one direction and blocked in the other direction. The exemplary wedge-shaped toothing visible in FIG. 3 translates the rotation of the toothed disk into a combined axial and rotational movement, with tangential force components leading to a torque on the device housing that may be determined and exploited independently from the axial injection force component.

Figure 4:
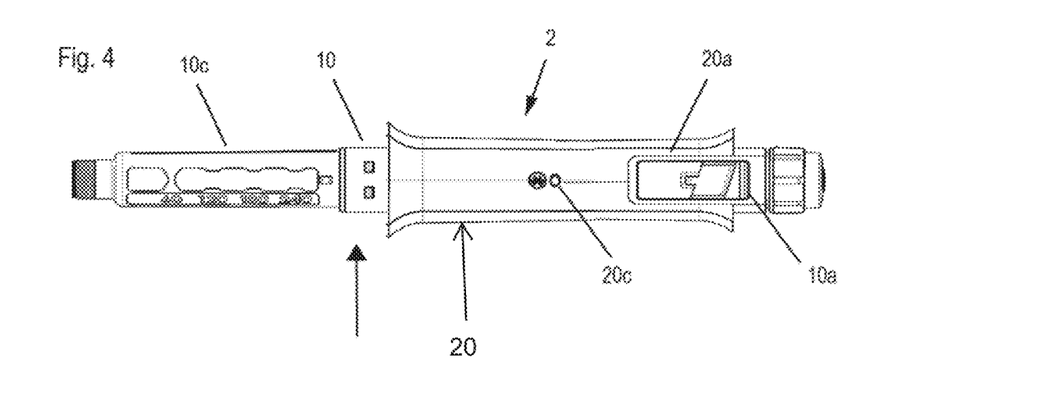
FIG. 4 depicts a detachable electronic module with an alternative housing.

FIG. 4 depicts an alternative to the proximally mounted module shown in FIGS. 2a-2b, with the force sensor included in an electronic module 2 with an essentially tubular module housing I that, when properly mounted, surrounds the injection device 1. In this case, the axial injection force is coupled, or transmitted, to the force sensor via a protrusion or recess in the device housing 10 presenting a radially oriented surface. Specifically, the flange-type annular step formed between the carpule holder 10c and the device housing 10 as indicated by the vertical arrow in FIG. 4 may be used to that purpose, obviously necessitating a module housing extending somewhat further in distal direction than the one shown. A counteracting force is transmitted to the force sensor from the hand of the user via the module housing. In this case, care has to be taken that the motion of the module housing relative to the device housing is not impeded in any way. A correspondingly floating module housing may be obtained by means of ball bearings. Provision of plural force sensors, evenly distributed about the circumference, may prevent an asymmetrical, off-axis movement of the module housing. A module housing surrounding the injection device may also be suited for measuring a torque transmitted from the user to the device upon setting of a dose by turning the dosage knob. This may even provide for a back-up, or redundant, way of counting dialing and/or expel dosage units.

The module housing 20 is designed to be positioned on the injection device housing in such a way as to neither interfere with the dial-and-dose components nor obscure any display window or visual indicator of the device. To this purpose, the module housing has a recess or cut-out 20a that matches with the window 10a. Hence the patient may continue using the injection device in a known manner, despite the presence of the electronic module, with all device interface elements remaining fully accessible throughout the handling sequence. Specifically, in this case the electronic module excludes the presence of a mechanical sensor to mechanically detect a rotation angle or linear shift of the dosing knob. Likewise, the electronic module excludes the presence of an optical sensor to read a dialed dose from a dialing sleeve. Ultimately, the module housing does not have to be rotationally symmetrical as shown in FIG. 4, but may feature a prominent nose or other protrusion for accommodating the electronic unit.

In another alternative to the location of the force sensor in a proximally mounted module as shown in FIGS. 2s-2b, and in accordance with the aforementioned variant one, the electronic unit may be incorporated in the injection device. Suitable locations for positioning a force sensor for expel click detection include a space between cartridge holder and cartridge, between a flange arranged on a distal end of the threaded rod and a stopper in the carpule, or between discharge button and coupling sleeve. The processing unit and the transmitter unit in this variant may be arranged in other suitable locations close to or remote from the force sensor.

Figure 5:
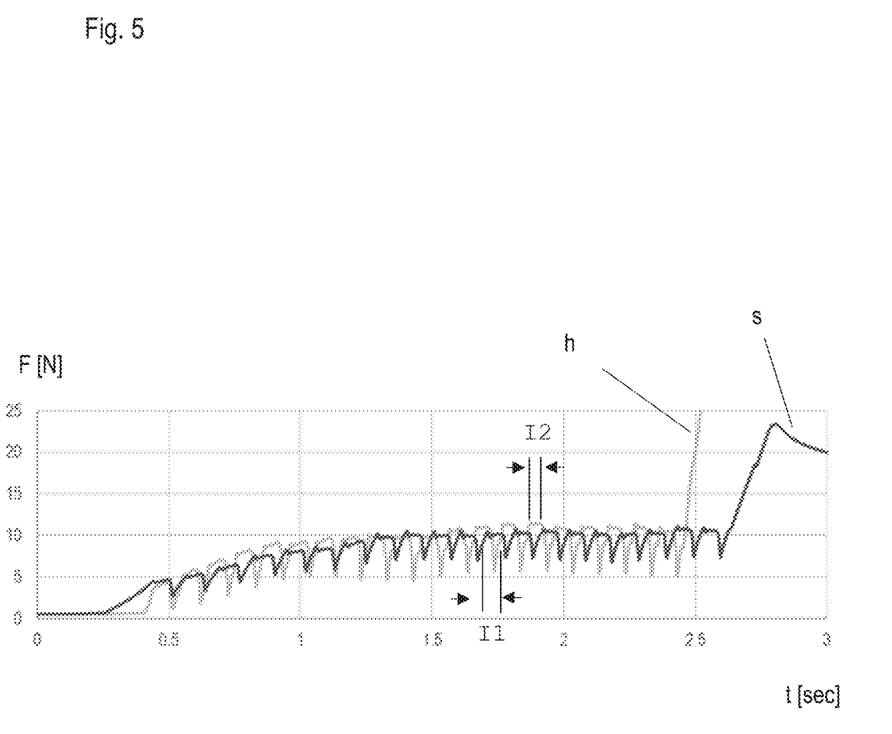
FIG. 5 depicts an axial injection force profile in arbitrary units as a function of time.

FIG. 5 depicts an axial injection force profile measured in a laboratory set-up for 20 dosage units expelled at 10 units/sec into air. The force sensor is embedded in an electronic module mounted at a proximal end between the release button and the thumb of a user as depicted in FIG. 2b. The thumb is approximated by a soft, elastic adapter element (dark line, labeled "s") or a hard, rigid adapter element (bright line, labeled "h"). A slower initial increase in the force profile and a minor delay at the end is observed for the soft adapter, otherwise both adapters appear equally suitable. By way of interpolation, a real human thumb with intermediate elastic properties is expected to give rise to a similar force profile. In both profiles, intervals comprising a gradually increasing and an at least approximately constant axial force component exhibiting little signal noise are clearly distinguishable. In both profiles, an exemplary interval I1, I2 of a duration of approximately 0.05 sec has been marked. The intervals correspond to the charging (loading) of the resilient element, specifically of the expel click spring of FIG. 3, and/or to a charged state prior to release thereof. The intervals precede a sharp decrease in the force signal followed by the gradual increase, which is reminiscent of a heavily oscillating and rapidly decaying vibration burst. The detailed shape of the force signal in the intervals is dependent on the specific design of the feedback elements moving relative to each other, such as a steepness of the wedge-shaped toothing of the toothed disk of FIG. 3, and the existence of a plateau with no or little slope following the wedge and preceding the instantaneous discharge of the expel click-spring. It is apparent from FIG. 5 that as little as 50 samples per second will allow to reasonably approximate the force profile and to identify the preparatory activities through their characteristic force profile intervals. The identification of the intervals of interest may take place in a consolidated manner at the end of the injection process on an entire force profile, or in real-time on an incoming data stream.

While the invention has been described in detail in the drawings and foregoing description, such description is to be considered illustrative or exemplary and not restrictive. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. The mere fact that certain elements or steps are recited in distinct claims shall not preclude the existence of further meaningful combinations of these elements or steps.

LIST OF REFERENCE NUMERALS 1 injection device
10 device housing
10c carpule holder
10e device cap
10f piston rod guide
10g grating
13c carpule
14a indicator sleeve
14b dosing sleeve
14c dosing knob
14d discharge button
15a coupling sleeve
15b annular flange
15c dosing click-spring
16a piston rod
16c threaded nut
16d flange
19a flexible arm
19b toothed disk
19c toothing
19d expel click-spring
2 electronic module
20 module housing
20c system status indicator
3 mobile device
31 patient
32 data server
4 electronic unit
41 mechanical feedback sensor
42 processing unit
43 transmitter unit
44 data storage unit

What is claimed is:

1. An electronic module adapted to be detachably attached to an injection device for monitoring an injection process performed by means of the-injection device, the injection device comprising:
feedback means that produce a number of successive mechanical feedback events proportionate to a dose of drug being expelled from the injection device,
wherein the electronic module comprises:
an orientation sensor adapted to measure an azimuth angle of an axis of the injection device and vibrational movement of the injection device in a plane perpendicular to the direction of gravity when the electronic module is attached to the injection device, wherein the orientation sensor prepares an azimuth angle signal output at a sampling rate of less than 2 kHz; and
a processing unit configured to receive the azimuth angle signal output by the orientation sensor and identify a dosage unit expelling event based on the signal output and also on the measured vibrational movement of the injection device in a plane perpendicular to the direction of gravity and wherein the processing unit is further configured to count the number of dosage unit expelling events to determine an expelled dose.

2. The electronic module of claim 1, wherein the orientation sensor is a multiple-axis gyroscope arranged in the electronic module.

3. The electronic module of claim 2, wherein the gyroscope is manufactured with Microelectromechanical systems technology.

4. The electronic module of claim 1, wherein the module comprises: a status indicator for indicating a device status of the injection device to a user or for indicating a lapse of a holding time following completion of a drug being expelled, a connection status from the electronic module to a mobile device, a module status of the electronic module or a process status of the overall injection process, or a process status of an injection device handling process.

5. The electronic module of claim 4, wherein the status indicator comprises light emitting diodes in traffic-light colors and/or an audible signal generator for generating language-independent beep sounds or melodies.

6. The electronic module of claim 1, wherein the module comprises a data storage unit for storing at least a timing and a quality information of the injection process.

7. The electronic module of claim 1, wherein the orientation sensor is adapted to measure the azimuth angle by determining an orientation of the injection device relative to a reference direction in a plane perpendicular to the direction of gravity.

8. The electronic module of claim 1, wherein the module further comprises a status indicator for indicating a device status to a user, comprising a positive confirmation of a dose having been set or corrected.

9. The electronic module of claim 1, wherein the electronic module is devoid of, a display, screen, or projector for visually transmitting readable instructions.

10. The electronic module of claim 1, wherein the module comprises a wireless communication unit connected to the processing unit, and adapted to wirelessly communicate injection information to a mobile device.

11. The electronic module of claim 10, wherein the injection information includes at least a time stamp and the dose of drug expelled, indicative of a time and quantity of injected medication.

12. The electronic module of claim 1, wherein the azimuth angle signal output is prepared at a sampling rate of less than 1 kHz.

13. The electronic module of claim 1, wherein the orientation sensor is a three-axis gyroscope producing concurrently three output signals indicative of an absolute orientation of the injection device.

* * * * *

UNITED STATES PATENT AND TRADEMARK OFFICE
CERTIFICATE OF CORRECTION

PATENT NO. : 11,534,556 B2
APPLICATION NO. : 16/585073
DATED : December 27, 2022
INVENTOR(S) : Ursina Streit et al.

It is certified that error appears in the above-identified patent and that said Letters Patent is hereby corrected as shown below:

In the Specification

In Column 1, Line 7, delete ""PC/IB2018/052114"" and replace with --PCT/IB2018/052114--

Signed and Sealed this
Sixteenth Day of April, 2024

Katherine Kelly Vidal
Director of the United States Patent and Trademark Office